(12) United States Patent
Brennan

(10) Patent No.: US 7,091,249 B2
(45) Date of Patent: Aug. 15, 2006

(54) DRUGS FOR SPINAL ANESTHESIA

(75) Inventor: Timothy J. Brennan, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 805 days.

(21) Appl. No.: 10/033,632

(22) Filed: Dec. 26, 2001

(65) Prior Publication Data

US 2003/0130308 A1 Jul. 10, 2003

(51) Int. Cl.
  *A01N 43/90* (2006.01)
  *A61K 31/47* (2006.01)

(52) U.S. Cl. ..................... 514/816; 514/307
(58) Field of Classification Search ............... 424/400; 514/816
See application file for complete search history.

(56) References Cited

U.S. PATENT DOCUMENTS 5,670,516 A * 9/1997 Arnold et al. ............... 514/307

OTHER PUBLICATIONS

Conn M.D., Howard F., Current Therapy Latest Approved Methods of Treatment For The Practicing Physician, 1977, W.B. Saunders Company, 825-831.*
Simmons, et al., "Kainate GluR5 receptor subtype mediates the nociceptive response to formalin in the rat", Neuropharmacology 37, pp. 25-36, (1998).

* cited by examiner

*Primary Examiner*—Sreeni Padmanabhan
*Assistant Examiner*—Konata M. George
(74) *Attorney, Agent, or Firm*—McKee, Voorhees & Sease, P.L.C.

(57) ABSTRACT

Spinal anesthetics for intrathecal administration to produce spinal anesthesia are provided with use of 6-[2-(1(2)H-tetrazole-5-yl)ethyl]decahydroisoquinolone-3-carboxylic acid or a pharmaceutically active analogue or its pharmaceutically active analogs.

5 Claims, 4 Drawing Sheets

Bupivacaine
Time (min)

Invention
Time (min)

Time After Injection

DRUGS FOR SPINAL ANESTHESIA

GRANT REFERENCE

This application was funded in part of the National Institute of Health under Grant No. GM55831.

FIELD OF THE INVENTION

This invention relates to spinal anesthetics.

BACKGROUND OF THE INVENTION

Spinal anesthesia has obvious advantages. However, spinal anesthesia, using local anesthetics, is associated with acute side effects including hypotension and urinary retention, persistent sequelae like transient neurologic symptoms (TNS) and on occasion permanent deficits like cauda equina syndrome. Current research in spinal anesthesia has focused on the incidence of TNS and the dose and particular local anesthetic used, the effect of additives like epinephrine, and associated factors like patient position. There has been no recent progress in advancing new drugs for spinal anesthesia. This invention moves forward in the direction of new drugs for spinal anesthesia.

One alternative to conduction block for spinal anesthesia is blockade of synaptic transmission in the spinal cored. This could be accomplished by activation of inhibitory receptors or by antagonism of excitatory receptors. Glutamate is the major excitatory central nervous system neurotransmitter. Glutamate activates ionotropic excitatory amino acid (EAA) receptors that are highly prevalent in the nervous system and transmit information through both N-methyl-D-aspartate (NMDA) as well as nonNMDA EAA receptors. Ketamine, a drug used clinically in anesthesia, antagonizes NMDA receptors. Thus far, a clinical use for nonNMDA receptor antagonists, blocking alpha-amino-3-hydroxy-5-methyl-4-isoxazole-propionic acid (AMPA) and kainate receptors, has not been discovered. In experimental animals, spinally administered non-NMDA receptor antagonists have been shown to inhibit nociception and produce motor dysfunction (Zahn P K, Umali E, Brennan T J: Intrathecal non-NMDA excitatory amino acid receptor antagonists inhibit pain behaviors in a rat model of postoperative pain, Pain 1998; 74: 213–23; Pogatzki E M, Zahn P K, Brennan T J; Effect of pretreatment with intrathecal excitatory amino acid receptor antagonists on the development of pain behavior caused by plantar incision. Anesthesiology 2000; 93: 489–96). This effect likely results from antagonism of nonNMDA receptors on dorsal horn sensory neurons as well as motor neurons in the ventral horn of the spinal cord.

Through drug development, more potent and specific nonNMDA receptor antagonists like 6-[2-(1(2)H-tetrazole-5-yl)ethyl]decahydroisoquinoline-3-carboxylic acid have been discovered. The observations of these literature references are perhaps why new drug investigations have gone in different directions than such specific nonNMDA receptors.

This inventor has discovered a more potent and specific nonNMDA receptor antagonist which is highly effective for spinal anesthesia and without the normal associated acute side effect of hypotension. The specific object of this invention is therefore the development of this spinal anesthetic and its successful use.

SUMMARY OF THE INVENTION

A method and composition for inducing spinal anesthesia without associated acute side effects. The method involves administering, preferably intrathecally 6-[2-(1(2)H-tetrazole-5-yl)ethyl]decahydroisoquinoline-3-carboxylic acid or a pharmaceutically-active analogue thereof.

DETAILED DESCRIPTION OF THE INVENTION

Figure 1A:
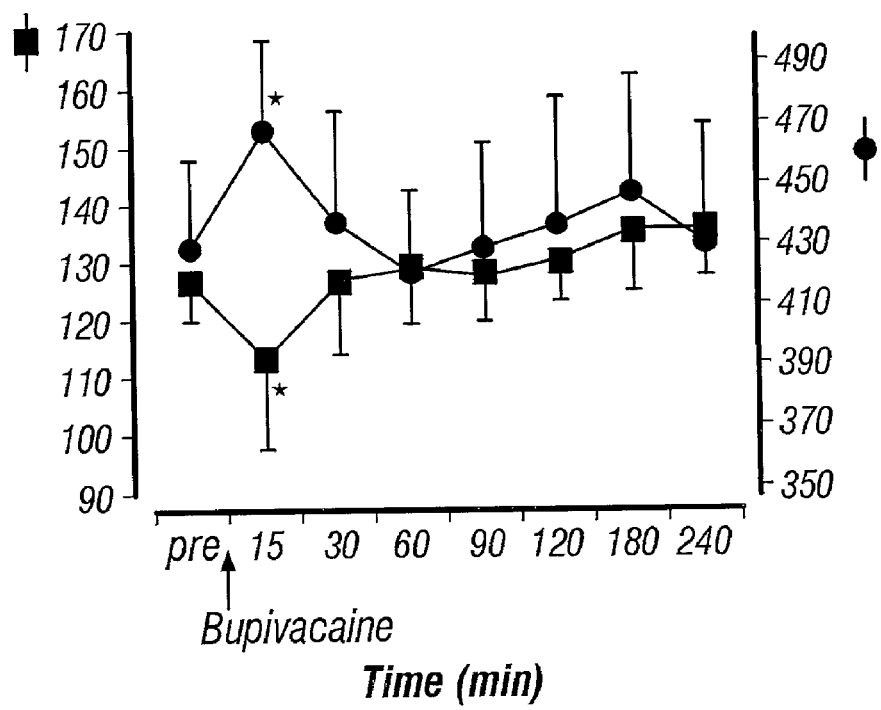
FIGS. 1–4 show the effects of treatments in accordance with the invention in comparison with intrathecal bupivacaine injection. They collectively demonstrate that the new drug is superior to a known local spinal anesthetic, and is without hypotension.

Preferred compounds for use in this invention are a class of receptor antagonists/drugs, i.e. the ampa-kainate receptor antagonists. AMPA is a-amino-3-hydroxy-5-methyl-4-isoxazole-propionic acid (AMPA) and kainate is a second subclass of these receptors. Another name for these receptors is nonNMDA ionotropic excitatory amino acid receptor antagonists. NMDA=N-methyl-D-aspartate. In particular, the most preferred compounds are 6-[2-(1(2)H-tetrazole-5-yl)ethyl]decahydroisoquinoline-3-carboxylic acid or its pharmaceutically acceptable analogues such as for example, salt forms. These specific compounds are known but have previously been reported by this inventor as having no effect on pain after incision by local infiltration of the drug active in the incision. This is further evidence of the surprising nature of their operativeness and effectiveness as spinal anesthetics. The compounds of the present invention may be administered with conventional local anesthetic carriers such as dextrose solution (8.25% dextrose in water, 5% dextrose in water, or 10% dextrose in water) and saline solution (0.9% saline).

The amount used to provide the desired spinal anesthetic effect will vary generally within the range of 0.1 mg to 3.0 mg, preferably 0.5 mg to 2.0 mg. Alternatively, the drug could be dosed by body weight. The amount used to provide the desired spinal anesthetic effect will vary generally within the range of 1 mg/kg to 60 mg/kg of body weight, preferably from 5 mg/kg to 40 mg/kg of bodyweight.

The specific AMPA kainate receptors used herein as an alternative to local anesthetics for spinal anesthesia are 6-[2-(1(2)H-tetrazole-5-yl)ethyl]decahydroisoquinoline-3-carboxylic acid or its pharmaceutically active analogues, such as salt forms. The formula for this compound in the carboxylic acid form is:

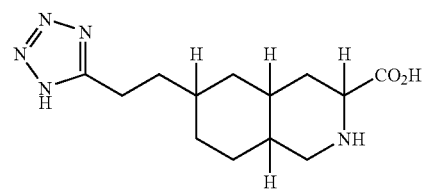

By pharmaceutically active analogues, applicant intends to define as within the scope of the invention modifications of the basic structure with moieties that do not alter the observed pharmaceutical properties.

The data of the following examples are offered to further illustrate but not limit the invention. The data of the examples demonstrate the use of the above-identified compounds as effective AMPA kainate receptors and effective spinal anesthetics.

EXAMPLES

Rats were tested before 15 minutes through 240 minutes after intrathecal injection of 5 nmoles (in 10 µl) of 6-[2-(1(2)H-tetrazole-5-yl)ethyl]decahydroisoquinoline-3-carboxylic acid. Sensory function was tested at the hindpaw using withdrawal response to pinprick and withdrawal to pinch with a sharp forceps. Motor performance (ambulation, the placing reflex and Rotarod time), blood pressure and heart rate was also evaluated. Some tests were repeated the next day. Responses after 6-[2-(1(2)H-tetrazole-5-yl)ethyl]decahydroisoquinoline-3-carboxylic acid were compared to injection of 40 µl of bupivacaine, 0.75%. Pinprick responses at the forepaw, chest, abdomen, hindleg and hindpaw were also examined after intrathecal 6-[2-(1(2)H-tetrazole-5-yl)ethyl]decahydroisoquinoline-3-carboxylic acid.

Intrathecal 6-[2-(1(2)H-tetrazole-5-yl)ethyl]decahydroisoquinoline-3-carboxylic acid blocked both sensory and motor responses through 180 minutes; complete recovery was present the following day. No change in blood pressure and heart rate occurred. The effects of 6-[2-(1(2)H-tetrazole-5-yl)ethyl]decahydroisoquinoline-3-carboxylic acid were more pronounced and sustained than bupivacaine. Segmental blockade of the response to pinprick was present after 6-[2-(1(2)H-tetrazole-5-yl)ethyl]decahydroisoquinoline-3-carboxylic acid.

Rats were anesthetized with halothane. The lumbar region was shaved, prepared with povidone-iodine, made kyphotic and incised 2 to 3 cm longitudinally in the midline at the level of the iliac crests. The space between the $5^{th}$ and $6^{th}$ lumbar vertebrae was punctured with 23G hypodermic needle and a 32G PU catheter (10 cm length, OD 0.0107 inches and ID 0.005 inches) reinforced with a Teflon coated stainless steel stylet (0.003 inches) was advanced through the needle cranially. The needle and the stylet were removed and the catheter withdrawn so that 6.5–7 cm extended outside of the lumbar masculature. The catheter was fixed to the fascia, sutured, inserted into an 8 cm length of PE-10 tubing and secured with glue covered with epoxy. The catheter was tunneled under the skin to the cervical region, flushed with saline and sealed with a cautery pen. The dead space of the catheter was 4.5 to 5 µl. The skin was closed and the rat was allowed to recover from anesthesia for 2–3 days.

For blood pressure measurement, the paratracheal region was shaved, prepared with povidone-iodine, and incised 1.5–2 cm longitudinally lateral to the midline. The carotid artery was isolated and cannulated with PE-50 tubing that had been stretched by exposing the distal end to heat. The catheter secured and tunneled subcutaneously to the posterior neck region. The skin was closed with 4–0 silk and the rat was allowed to recover for 2–3 days before experiments began.

The mean arterial pressure and heart rate were measured using the carotid artery catheter attached to a pressure transducer relayed to a polygraph and preamplifier (Grass, Quincy, Mass.). Heart rate was intermittently measured by counting the arterial pulse wave for 30 seconds.

First, the withdrawal response to pinprick was tested on each hindpaw. A 5 mm long tip of a safety pin attached to a von Frey filament (520 mN) was applied once to the plantar aspect of each hindpaw. Either a withdrawal response or a reaction occurred (1=positive response) or no withdrawal (0=no response). The sum of the scores (0, 1 or 2) for each rat was recorded. If no response or reaction was elicited by pinprick, a serrated dissecting forceps was used to pinch the skin of the plantar region for 2–3 sec. Again, withdrawal or reaction was considered a positive response (score=1) and the absence of both a negative test (score=0). In preliminary studies, after drug administration, some rats did not respond to pinprick but responded to pinch, but all rats that did not respond to pinch also failed to respond to pinprick. Because the response to pinch was quite vigorous and rats were subjected to repeated tests in a single day, only rats unresponsive to pinprick were tested for pinch. If pinprick evoked a response, pinch was designated as positive also. The sum of the scores after pinch (0, 1 or 2) was recorded.

In a separate group of rats (n=5), the response to pinprick was tested once on the left hindpaw, the left hindleg, the lower abdomen, the chest and the left forepaw in rats injected with intrathecal 6-[2-(1(2)H-tetrazole-5-yl)ethyl]decahydroisoquinoline-3-carboxylic acid. Withdrawal, muscle contraction, or attempted escape reaction to pinprick was considered a positive test whereas their absence was considered a negative response. This test was not blinded.

Withdrawal response to pinprick were also tested before and after infiltration of (50 nmoles in 100 µl) of 6-[2-(1(2)H-tetrazole-5-yl)ethyl]decahydroisoquinoline-3-carboxylic acid into the left hind paw (n=5). Responses were recorded before injection of 6-[2-(1(2)H-tetrazole-5-yl)ethyl]decahydroisoquinoline-3-carboxylic acid and at 15, 30 and 60 minutes after injection. This test was not blinded.

Rats were trained over a two-day period. Training began by placing the rat on a Rotarod (Stoelting, Wood Dale, Ill.) that was fixed for three minutes. Then, three series of trials separated by 2–3 hours were performed. During each trial, the rat was placed on the Rotarod accelerating for the first 20 s then at a constant rate of approximately 5 rpm, until a 180 s cut off time. If the rat fell at any time during the initial trial, the trial was repeated. Each rat was allowed three attempts per trial. On the second day, the same procedure was repeated, though acceleration was sustained for 120 s to approximately 12 rpm, with a 150 second cut off time. On day 3, the test day, rats are again placed on the Rotarod and accelerated for 120 seconds to 12 rpm with the cutoff time of 150 seconds. Each rat was permitted 4 attempts at 15 minute intervals. Those successful in 2 of the 4 attempts continued in the protocol, and the average of the 4 attempts was considered the baseline (pre). After a two-hour period, the test drug was administered and rats were examined once on the Rotarod at 30, 60, 90, 120, 180, and 240 minutes. They were again tested the following day (24 hrs.) Ambulation (walking) was observed for approximately 1 minute (2=normal; 1=limping; 0=paralyzed) once every test period after the Rotarod test. Then the placing reflex was tested. Rats were placed on a table and the dorsum of either hindpaw was drawn across the edge of the table; this elicits a lifting of the paw onto the surface of the table (2=normal; 1=delay of 1–2 sec.; 0=more than 2 sec.). This test was performed 3 times for each hindlimb after each ambulation test. The sum of the three trials on both paws were recorded (1–12).

The dose and volume of drugs injected intrathecally were determined from the dose required to produce hindlimb sensory and motor loss in preliminary experiments. Bupivacaine HCl (0.75% in 8.25% dextrose for spinal injection) was purchased from Abbott Laboratories (Chicago, Ill.). The intrathecal injection volume was 40 µl. The compound was dissolved in 10% dextrose and water. The injection volume was 10 μl. All intrathecal drug injections were followed by a flush of 10 μl preservative-free saline.

The Bupivacaine HCl was used because it is a known spinal anesthetic and therefore useful for comparison with the compounds of the present invention.

Figure 1B:
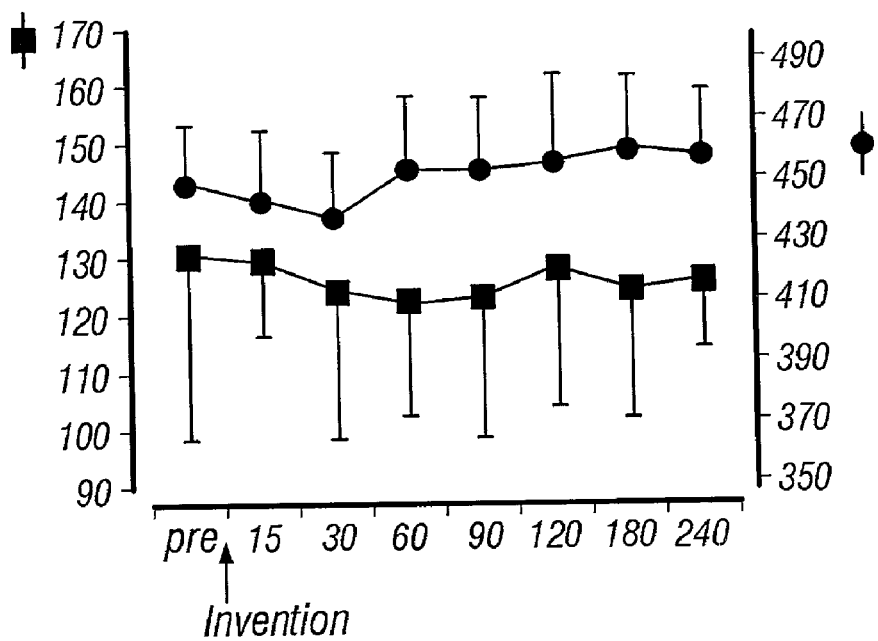

Fifteen minutes after intrathecal administration of bupivacaine (FIG. 1), mean arterial pressure decreased and heart rate increased (P<0.5 vs Pre). These changes were short-lived, resolving by 30 minutes. Intrathecal 6-[2-(1(2)H-tetrazole-5-yl)ethyl]decahydroisoquinoline-3-carboxylic acid did not change blood pressure or heart rate.

Figure 2A:
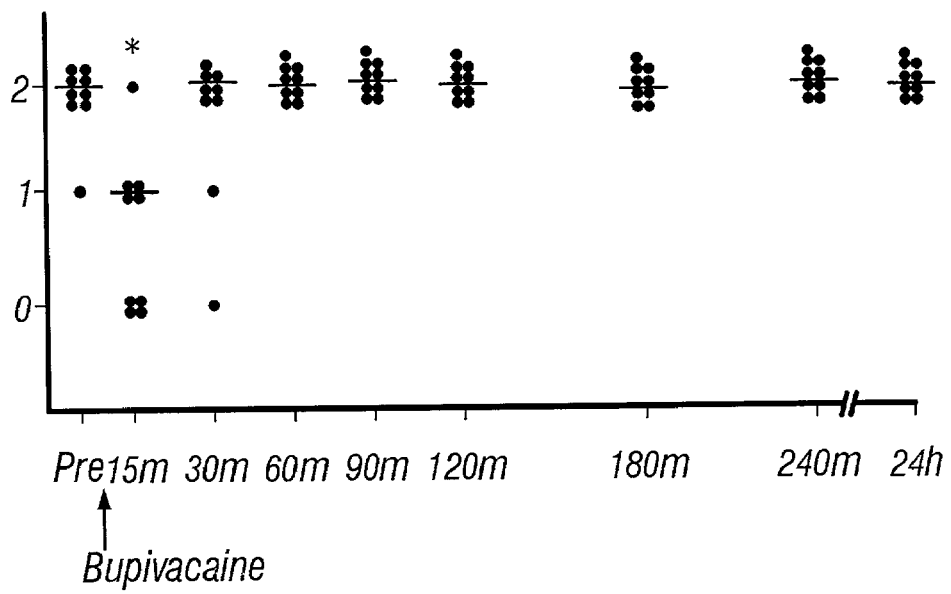
Figure 2B:
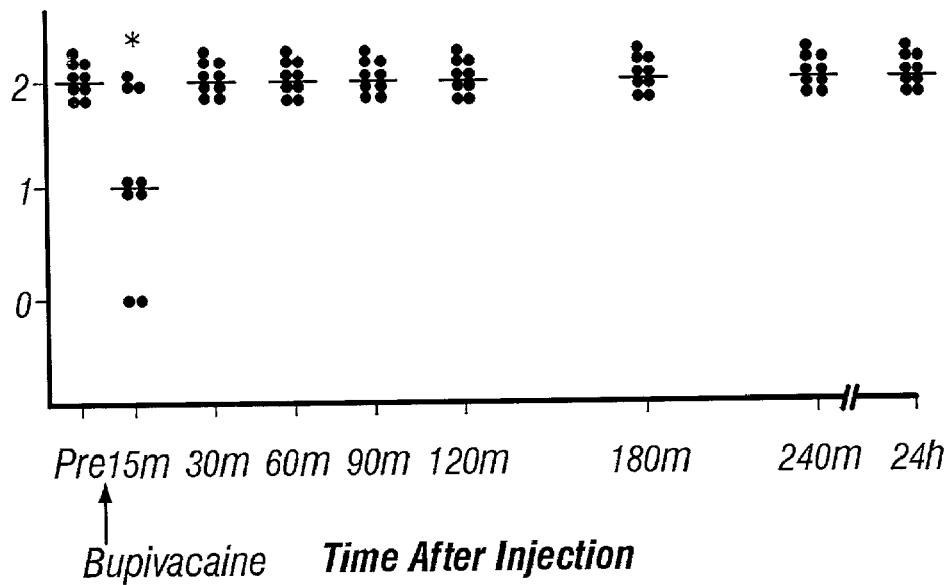

Ambulation, the placing reflex and rotorod performance (Table 1) were decreased for 30 minutes after intrathecal bupivacaine administration (P<0.05 vs Pre). Withdrawal to pinprick was reduced 15 minutes after bupivacaine injection (P<0.05 vs. Pre) but was not eliminated in all tests (FIG. 2). All rats had recovered 60 minutes later. The response to pinch was reduced 15 minutes after bupivacaine injection (P<0.05 vs Pre) with full recovery at 30 minutes and thereafter.

6-[2-(1(2)H-tetrazole-5-yl)ethyl]decahydroisoquinoline-3-carboxylic acid significantly impaired ambulation from 15 minutes through 90 minutes (P<0.05 vs Pre). All rats had recovered by 4 hours. The placing reflex was completely eliminated in all rats through 90 minutes and impaired through 3 hours (P<0.05 vs. Pre). Rotorod performance was decreased through 4 hours after 6-[2-(1(2)H-tetrazole-5-yl)ethyl]decahydroisoquinoline-3-carboxylic acid injection (P<0.05 vs. Pre); full recovery was evident the next day.

Figure 3A:
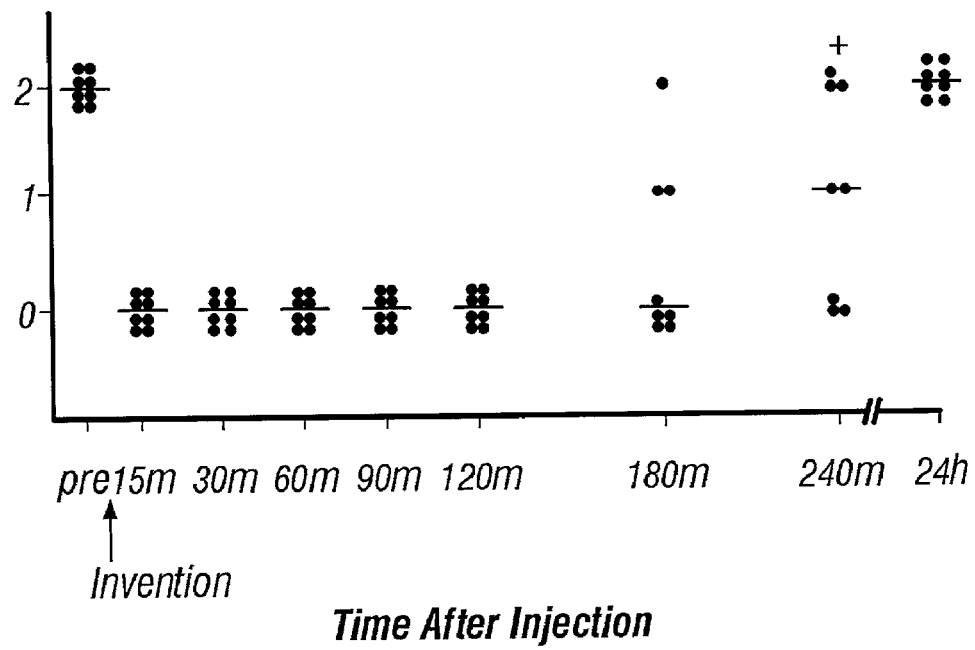
Figure 3B:
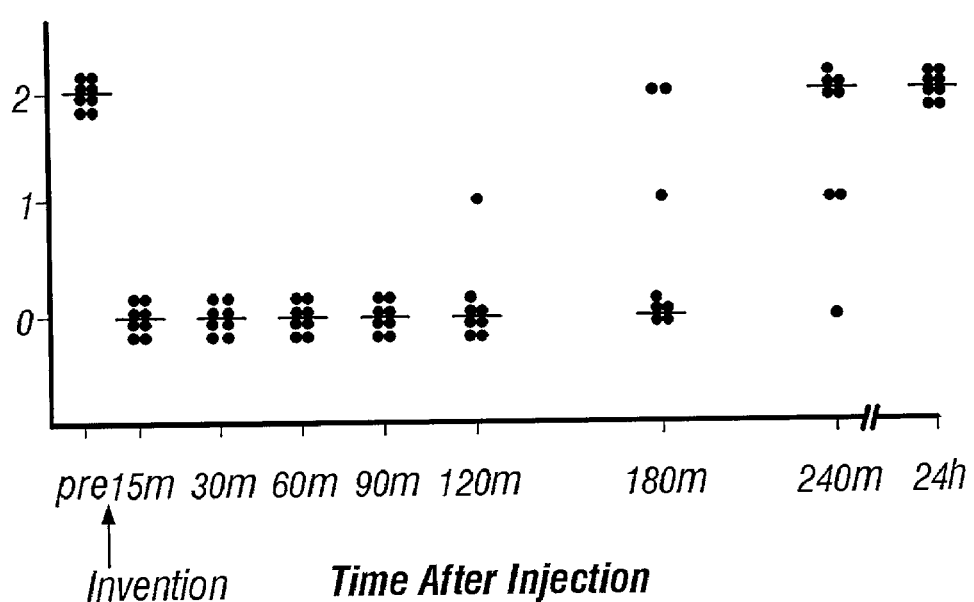
Figure 4:
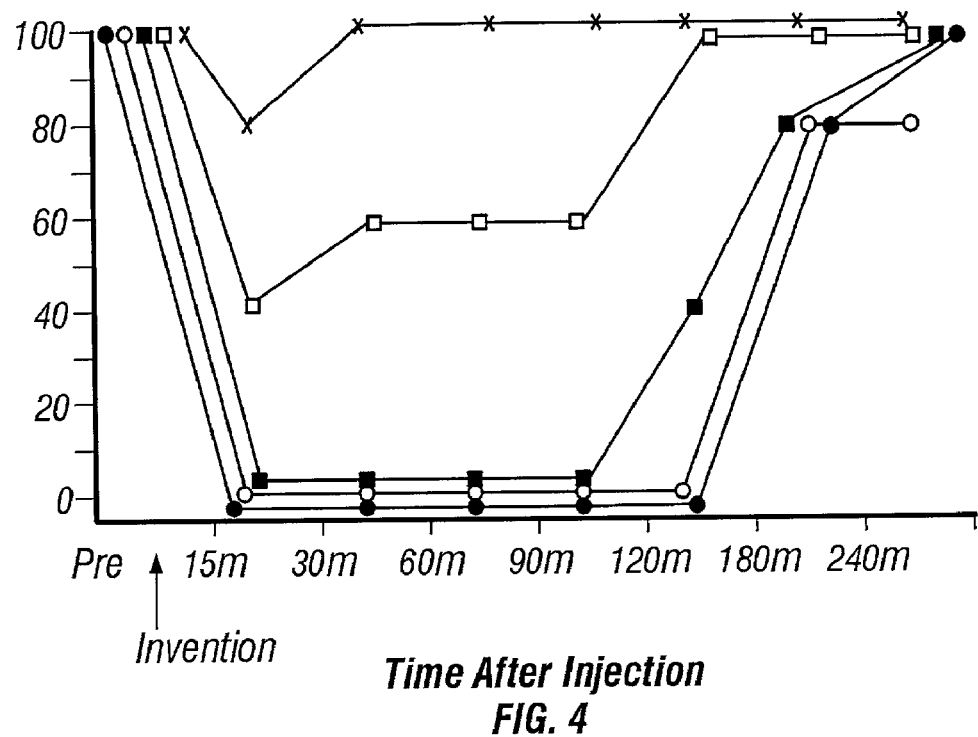

After intrathecal 6-[2-(1(2)H-tetrazole-5-yl)ethyl]decahydroisoquinoline-3-carboxylic acid rats failed to respond to pin prick (FIG. 3) from 15 minutes through 2 hours (P<0.05 vs. Pre). Similarly, all rats failed to respond to pinch from 15 through 90 minutes (P<0.05 vs Pre). These nociceptive responses recovered fully the next day. 6-[2-(1(2)H-tetrazole-5-yl)ethyl]decahydroisoquinoline-3-carboxylic acid produced greater motor deficits than bupivacaine (P<0.05) from 30 minutes through 3 hours in all tests of motor function. 6-[2-(1(2)H-tetrazole-5-yl)ethyl]decahydroisoquinoline-3-carboxylic acid produced greater inhibition of pinprick and pinch (P<0.05) than bupivacaine through 3 and 4 hours, respectively. No rats vocalized or appeared agitated in response to pinprick or pinch after either drug.

Pinprick testing at the hindpaw, leg, abdomen, chest and forepaw demonstrated that intrathecal 6-[2-(1(2)H-tetrazole-5-yl)ethyl]decahydroisoquinoline-3-carboxylic acid blocked sensation below the chest in all rats through 90 minutes, and in the hindlimb through 120 minutes. There was evidence of sensory block of the forelimb in only one test at 15 minutes.

When 6-[2-(1(2)H-tetrazole-5-yl)ethyl]decahydroisoquinoline-3-carboxylic acid was injected into the hind paw there was no change in response from baseline. All five rats withdrew to pinprick at 15, 30 and 60 minutes (data not shown).

TABLE 1

Effect of IT LY293558 and bupivacaine on motor function

| Time | Cumulative Placing Score | Ambulation Score | Rotarod Time (sec) |
|---|---|---|---|
| LY293558 5 nmoles | | | |
| Pre | 12 (12-12) | 2 (2-2) | 144 ± 10 |
| 15 min | 0 (0-0)*† | 0 (0-0)* | 3 ± 4* |
| 30 min | 0 (0-0)*† | 0 (0-0)*† | 3 ± 0*† |
| 60 min | 0 (0-0)*† | 0 (0-0)*† | 7 ± 12*† |
| 90 min | 0 (0-0)*† | 0 (0-1)*† | 7 ± 14*† |
| 120 min | 1.5 (0-11)*† | 1 (1-2)† | 11 ± 13*† |
| 180 min | 11 (3-12)*† | 2 (1-2)† | 68 ± 29*† |
| 240 min | 12 (8-12)† | 2 (2-2) | 115 ± 42* |
| 24 hrs | 12 (12-12) | 2 (2-2) | 149 ± 5 |
| Bupivacaine 0.75% | | | |
| Pre | 12 (12-12) | 2 (2-2) | 146 ± 8 |
| 15 min | 0 (0-0)* | 0 (0-0)* | 5 ± 6* |
| 30 min | 6 (0-12)* | 1 (0-2)* | 49 ± 42* |
| 60 min | 12 (1-12) | 2 (1-2) | 135 ± 43 |
| 90 min | 12 (0-12) | 2 (1-2) | 136 ± 39 |
| 120 min | 12 (12-12) | 2 (2-2) | 137 ± 26 |
| 180 min | 12 (12-12) | 2 (2-2) | 142 ± 15 |
| 240 min | 12 (12-12) | 2 (2-2) | 149 ± 2 |
| 24 hrs | 12 (12-12) | 2 (2-2) | 150 ± 0 |

Tests for motor impairment before drug injection (Pre) and 15 to 240 min. and 24 hrs. after intrathecal administration of LY293558 (n = 8) or bupivacaine (n = 8). Placing reflex and ambulation are expressed as median and range. Rotarod time is expressed median and range. Rotarod time is expressed as mean ± standard deviation.
*P<0.05 vs. Pre by Friedman and Dunnett's test.
†P<0.05 vs. bupivicaine by Mann-Whitney rank sum test.

Intrathecally administered 6-[2-(1(2)H-tetrazole-5-yl)ethyl]decahydroisoquinoline-3-carboxylic acid produced reversible, sustained sensory and motor blockade of the hindlimbs in rats. Bupivacaine decreased sensory and motor responses, but the effect of 6-[2-(1(2)H-tetrazole-5-yl)ethyl]decahydroisoquinoline-3-carboxylic acid was more pronounced and prolonged. These data indicate that other nonNMDA receptor antagonists like 6-[2-(1(2)H-tetrazole-5-yl)ethyl]decahydroisoquinoline-3-carboxylic acid may be useful for producing spinal anesthesia in humans.

Clinically, intrathecally-administered local anesthetics produce spinal anesthesia by interfering with axonal conduction of the sensory and motor nerve roots. A contribution by blockade of synaptic transmission and/or conduction within the spinal cord by local anesthetics may also occur. Conduction blockade does not likely contribute to the sensory and motor deficits caused by intrathecal 6-[2-(1(2)H-tetrazole-5-yl)ethyl]decahydroisoquinoline-3-carboxylic acid because infiltration with 50 nmoles in 100 μl 6-[2-(1(2)H-tetrazole-5-yl)ethyl]decahydroisoquinoline-3-carboxylic acid did not affect the withdrawal response to pinprick.

Data for rats for intrathecal anesthetic use has been found predictive of similar responses in human patients.

What is claimed is:

1. A method of inducing spinal anesthesia, comprising:
   administering spinally a small but anesthesia producing amount of 6-[2-(1(2)H-tetrazole-5-yl)ethyl]decahydroisoquinoline-3-carboxylic acid or a pharmaceutically active analogue hereof to a patient in need of a spinal.

2. The method of claim 1 wherein the administering spinally is by intrathecal administration.

3. The method of claim 2 wherein 6-[2-(1(2)H-tetrazole-5-yl)ethyl]decahydroisoquinoline-3-carboxylic acid or a pharmaceutically active analogue is administered in conjunction with a pharmaceutically acceptable carrier for 6-[2-(1(2)H-tetrazole-5-yl)ethyl]decahydroisoquinoline-3-carboxylic acid or its biologically active analogue.

4. The method of claim 2 wherein the dose of 6-[2-(1(2)H-tetrazole-5-yl)ethyl]decahydroisoquinoline-3-carboxylic acid or a pharmaceutically active analogue administered is from 0.1 mg to 3.0 mg.

5. The method of claim 2 wherein the dose of 6-[2-(1(2)H-tetrazole-5-yl)ethyl]decahydroisoquinoline-3-carboxylic acid or a pharmaceutically active analogue administered is from 0.5 mg to 2.0 mg.

* * * * *

UNITED STATES PATENT AND TRADEMARK OFFICE
CERTIFICATE OF CORRECTION

| | | |
|---|---|---|
| PATENT NO. | : 7,091,249 B2 | Page 1 of 1 |
| APPLICATION NO. | : 10/033632 | |
| DATED | : August 15, 2006 | |
| INVENTOR(S) | : Brennan | |

It is certified that error appears in the above-identified patent and that said Letters Patent is hereby corrected as shown below:

Col. 1, Line 6:
ADD: after GM55831.  --The government has certain rights in this application.--

Col. 8, Line1:
DELETE:  after analogue "hereof"
ADD:  after analogue --thereof--

Signed and Sealed this

Seventeenth Day of October, 2006

JON W. DUDAS
*Director of the United States Patent and Trademark Office*